United States Patent
Wu et al.

(10) Patent No.: US 9,494,512 B2
(45) Date of Patent: Nov. 15, 2016

(54) METHODS AND SYSTEMS FOR REMOTELY DETECTING HAZARDOUS MATERIALS USING ELECTROMAGNETIC ENERGY

(76) Inventors: Dong Ho Wu, Olney, MD (US); Rongjia Tao, Cherry Hill, NJ (US); Benjamin D. Graber, Washington, DC (US)

( * ) Notice: Subject to any disclaimer, the term of this patent is extended or adjusted under 35 U.S.C. 154(b) by 488 days.

(21) Appl. No.: 13/486,560

(22) Filed: Jun. 1, 2012

(65) Prior Publication Data

US 2012/0305773 A1   Dec. 6, 2012

Related U.S. Application Data

(60) Provisional application No. 61/492,610, filed on Jun. 2, 2011.

(51) Int. Cl.
| | | |
|---|---|---|
| *G01J 3/42* | (2006.01) | |
| *G01N 21/3581* | (2014.01) | |
| *G01N 33/00* | (2006.01) | |
| *G01V 8/00* | (2006.01) | |
| *G01N 21/17* | (2006.01) | |
| *G01N 21/3504* | (2014.01) | |

(52) U.S. Cl.
CPC ...... *G01N 21/3581* (2013.01); *G01N 33/0057* (2013.01); *G01V 8/005* (2013.01); *G01N 21/3504* (2013.01); *G01N 2021/1793* (2013.01); *G01N 2021/1795* (2013.01)

(58) Field of Classification Search
CPC .................. G01N 21/3581; G01N 21/3586; G01N 21/359
USPC ............................ 250/339.01, 339.06, 341.1
See application file for complete search history.

(56) References Cited

U.S. PATENT DOCUMENTS

| | | | |
|---|---|---|---|
| 4,451,736 A | | 5/1984 | Cameron |
| 5,078,952 A | | 1/1992 | Gozani et al. |
| 5,286,973 A | * | 2/1994 | Westrom et al. ............. 250/253 |
| 5,939,721 A | | 8/1999 | Jacobsen et al. |
| 6,078,047 A | * | 6/2000 | Mittleman et al. ........ 250/338.1 |
| 6,234,006 B1 | | 5/2001 | Sunshine et al. |
| 6,281,502 B1 | * | 8/2001 | Pineau et al. ............. 250/361 R |
| 6,448,562 B1 | | 9/2002 | Seidler et al. |
| 6,480,141 B1 | * | 11/2002 | Toth et al. ...................... 342/22 |

(Continued)

FOREIGN PATENT DOCUMENTS

WO   WO 2008-091400   7/2008

OTHER PUBLICATIONS

International Search Report for PCT/US2010/023316 mailed Jun. 15, 2011.

(Continued)

*Primary Examiner* — David Porta
*Assistant Examiner* — Djura Malevic
(74) *Attorney, Agent, or Firm* — RatnerPrestia

(57) ABSTRACT

Systems and methods for remotely detecting nuclear and non-nuclear materials such as chemical agents and gas-phase explosives are disclosed. Nuclear and non-nuclear materials may be detected by transmitting electromagnetic energy toward a remote target area, collecting scattered electromagnetic energy reflected from the remote target area, analyzing an absorption spectrum of the collected scattered electromagnetic energy, and detecting a presence of at least one nuclear or non-nuclear material in the remote target area based on the analyzed absorption spectrum.

22 Claims, 7 Drawing Sheets

(56) References Cited

U.S. PATENT DOCUMENTS

| | | | |
|---|---|---|---|
| 6,605,808 B2* | 8/2003 | Mickan et al. | 250/341.8 |
| 6,701,772 B2 | 3/2004 | Kreichauf et al. | |
| 6,777,684 B1* | 8/2004 | Volkov et al. | 250/341.1 |
| 7,015,475 B2* | 3/2006 | Hailey | 250/358.1 |
| 7,098,463 B2 | 8/2006 | Adamovics | |
| 7,100,424 B2 | 9/2006 | Wilson | |
| 7,120,226 B2 | 10/2006 | Ledoux et al. | |
| 7,188,513 B2* | 3/2007 | Wilson | 73/31.05 |
| 7,358,863 B2* | 4/2008 | Haney | 340/907 |
| 7,378,658 B2* | 5/2008 | Mueller et al. | 250/358.1 |
| 7,385,549 B2* | 6/2008 | Lovberg et al. | 342/22 |
| 7,579,845 B2* | 8/2009 | Peschmann et al. | 324/637 |
| 7,728,296 B2* | 6/2010 | Cole et al. | 250/338.1 |
| 8,129,684 B2* | 3/2012 | Mueller | 250/341.8 |
| 8,247,775 B2* | 8/2012 | Patel et al. | 250/341.1 |
| 8,620,132 B2* | 12/2013 | Rahman et al. | 385/147 |
| 8,806,914 B2* | 8/2014 | Brasfield | 73/23.34 |
| 8,890,077 B2* | 11/2014 | Rosson et al. | 250/361 R |
| 9,046,619 B2* | 6/2015 | Blackburn et al. | |
| 2001/0033636 A1* | 10/2001 | Hartick et al. | 378/88 |
| 2005/0082479 A1* | 4/2005 | Wallace et al. | 250/330 |
| 2006/0022140 A1* | 2/2006 | Connelly et al. | 250/338.1 |
| 2006/0169025 A1* | 8/2006 | Wilson | 73/31.03 |
| 2006/0255277 A1* | 11/2006 | Cole et al. | 250/341.1 |
| 2007/0145276 A1 | 6/2007 | Zhang et al. | |
| 2008/0283761 A1 | 11/2008 | Robinson et al. | |
| 2008/0319321 A1* | 12/2008 | Goldbach | 600/475 |
| 2009/0086877 A1* | 4/2009 | Hagelstein et al. | 376/100 |
| 2009/0146060 A1* | 6/2009 | Farshi | 250/339.06 |
| 2009/0314943 A1* | 12/2009 | Breit et al. | 250/341.1 |
| 2010/0290487 A1* | 11/2010 | Wu | 372/21 |
| 2010/0326216 A1* | 12/2010 | Nacson | 73/864.35 |
| 2011/0273708 A1* | 11/2011 | Tong | 356/312 |

OTHER PUBLICATIONS

International Search Report for PCT/US2012/040439 mailed Feb. 26, 2013.
International Preliminary Report on Patentability for PCT/US2012/040439 issued Dec. 2, 2013.
Office Action for U.S. Appl. No. 13/148,120 mailed Jul. 22, 2014.
Final Office Action for U.S. Appl. No. 13/148,120 mailed Aug. 13, 2015.
U.S. Office Action for U.S. Appl. No. 13/148,120, dated Aug. 19, 2016, 16 pages.

* cited by examiner

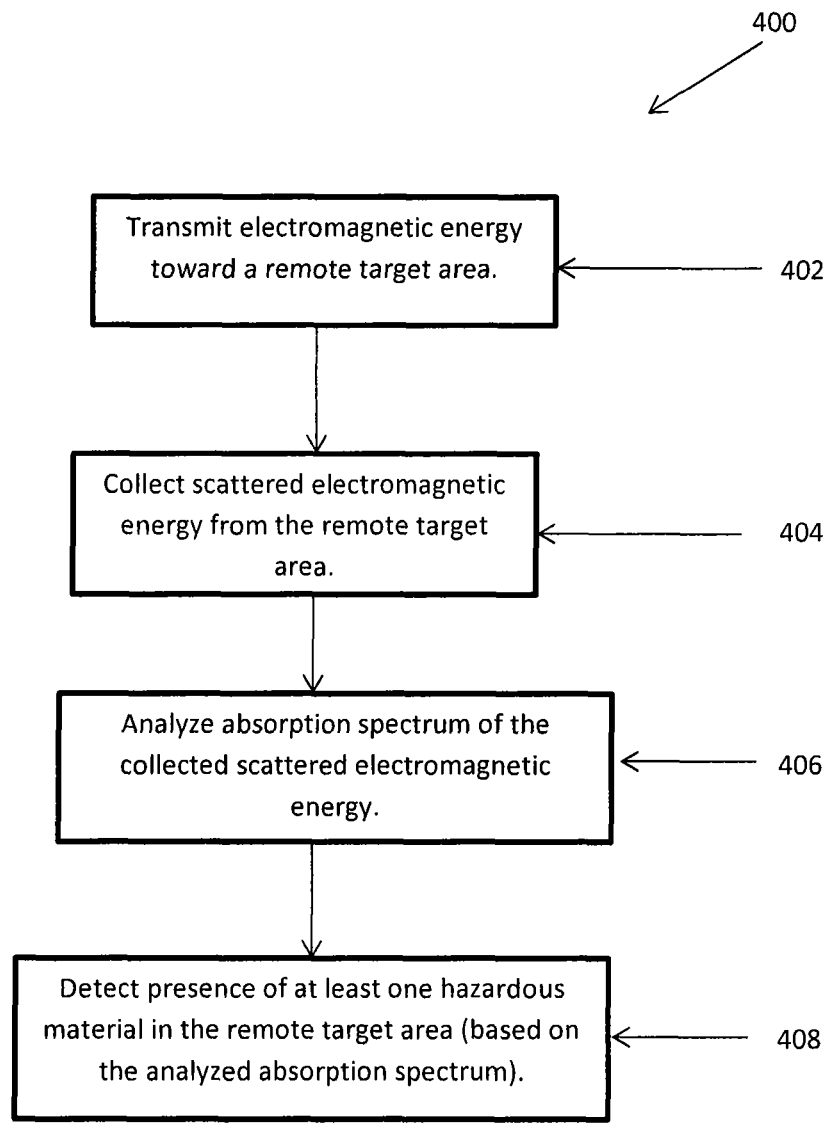

METHODS AND SYSTEMS FOR REMOTELY DETECTING HAZARDOUS MATERIALS USING ELECTROMAGNETIC ENERGY

CROSS REFERENCE TO RELATED APPLICATIONS

The present application is related to U.S. Provisional Patent Application Ser. No. 61/492,610 entitled METHOD FOR REMOTE DETECTION OF NUCLEAR MATERIALS AND CHEMICAL AGENTS USING ACTIVE MILLIMETER-WAVE AND FAR-INFRARED SPECTROSCOPY filed on Jun. 2, 2011, the contents of which are incorporated fully herein by reference.

FIELD OF THE INVENTION

The present invention relates to methods and systems for detecting concealed hazardous materials such as nuclear materials, chemical agents, and gas phase explosives.

BACKGROUND OF THE INVENTION

Detection of hazardous materials is important for national security and defense. There are typically two conventional approaches to the detection of hazardous materials: passive techniques and active interrogation techniques.

Conventional passive techniques can be used to detect nuclear material, for example, by direct measurement of the nuclear radiation, mainly gamma rays and neutrons. However, there are many disadvantages with respect to conventional passive detecting techniques. For example, conventional passive techniques are typically heavy, bulky, and expensive for a long distance remote detection. Moreover, conventional detectors using passive techniques cannot detect shielded nuclear material at remote distances. Also, because passive methods rely on the direct detection of gamma rays and neutrons, which cannot be done from a significant distance (>100 m), a user of a passive technique can be exposed to a high dose of radiation.

Conventional active interrogation techniques, which use neutron, gamma ray, or muon beams, for example, are also used to detect hazardous materials. However, many disadvantages arise from the use of such conventional active techniques. These disadvantages include poor reliability and the potential to detonate a hazardous material such as a nuclear bomb located in a target area.

Due to the disadvantages of conventional passive and active methods to detect hazardous material, it is obvious that systems and methods to safely and remotely detect such material would be of great interest. The present invention, which will be discussed further below, provides such systems and methods.

SUMMARY OF THE INVENTION

The present invention is embodied in systems and methods for remotely detecting nuclear and non-nuclear materials such as chemical agents and gas-phase explosives are disclosed. Nuclear and non-nuclear materials may be detected by transmitting electromagnetic energy toward a remote target area, collecting scattered electromagnetic energy reflected from the remote target area, analyzing an absorption spectrum of the collected scattered electromagnetic energy, and detecting a presence of at least one nuclear or non-nuclear material in the remote target area based on the analyzed absorption spectrum.

BRIEF DESCRIPTION OF THE DRAWINGS

The invention is best understood from the following detailed description when read in connection with the accompanying drawings, with like elements having the same reference numerals. This emphasizes that according to common practice, the various features of the drawings are not drawn to scale. On the contrary, the dimensions of the various features are arbitrarily expanded or reduced for clarity. Included in the drawings are the following figures:

FIG. 4 is a flow chart depicting steps for remotely detecting at least one hazardous material in accordance with aspects of the present invention;

DETAILED DESCRIPTION OF THE INVENTION

Figure 1:
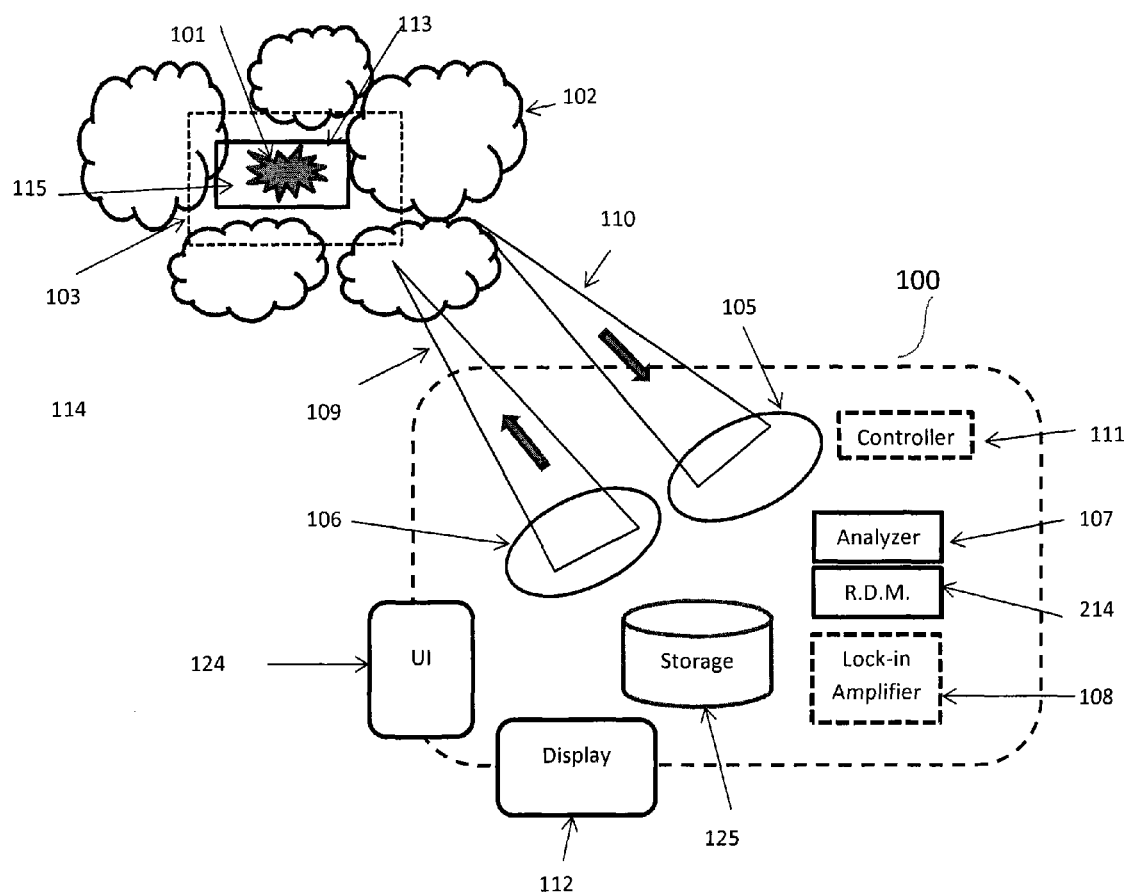
FIG. 1 is a block diagram illustrating a hazardous material detection system according to aspects of the present invention.

As a general overview, and as will be described in further detail below, the present invention relates to methods and systems for remotely detecting hazardous materials based on the analysis of changes in the atmosphere surrounding the hazardous materials. The hazardous materials described herein include nuclear materials and non-nuclear materials (e.g., chemical agents and gas-phase explosives). In one embodiment, an exemplary hazardous material detection system transmits electromagnetic (EM) energy toward a remote target area, collects scattered EM energy reflected from the remote target area, and analyzes the absorption spectrum of the scattered EM energy to detect the presence of hazardous materials in the target area. The present invention has broad applications for national security and defense.

Aspects of the present invention use an EM transmitter, detector, and analyzer to remotely sense hazardous materials. For nuclear materials, the nuclear materials ionize molecules and modify the chemical composition of the surrounding atmospheric molecules, for example, ozone formation and decomposition of water molecules in the air. Most air molecules (e.g., $H_2O$, $N_2$, $O_2$, and $CO_2$) have resonance frequencies within the millimeter-wave frequency range and the far-infrared frequency range. Since the ionization of these molecules and the alteration of the chemical composition change the resonance frequencies, these changes appear in the millimeter-wave and far-infrared (or terahertz) spectra of the air. Oxygen, nitrogen and water molecules in the air surrounding the nuclear materials generate unique signatures indicative of the nuclear materials when they interact with the ionizing effects of the nuclear materials. For chemical agents and explosive vapor on the other hand, when the chemical agents and/or explosive vapor are mixed with air molecules, they alter the chemical composition of air. The alternation of the chemical composition changes the resonance frequencies. These changes also appear in the millimeter-wave and far-infrared (or terahertz) spectra of the air. These characteristic signatures typically range from below about 50 GHz to 3 THz, which enables identification of hazardous material through infrared, far-infrared (e.g., terahertz), and/or millimeter-wave spectroscopy.

An advantage achieved by the present invention over conventional detection techniques is that the EM energy projected towards the target area is safe to humans. Therefore, unlike conventional active techniques, the present invention may be used to detect hazardous materials in target areas where humans are present. In addition, the distance for remote detection of the hazardous material is determined by the strength of the EM signal beam (i.e., the transmitted EM energy), not by the strength of the radiation produced by the nuclear material or by the amount of chemical agents or explosive vapor. Therefore, the detection of hazardous materials is only limited by the strength of the transmitted electromagnetic energy, which allows detection at distances of a few hundred meters (possibly a kilometer or more).

FIG. 1 is a block diagram illustrating an exemplary system 100 for remotely detecting hazardous material 101. The exemplary system 100 will be described below with reference to nuclear hazardous materials; however, the use of system 100 for detecting non-nuclear hazardous materials will be understood by one of skill in the art from the description herein. Nuclear material 101 may optionally be concealed in a shielded enclosure 113.

System 100 includes a transmitter 106 for transmitting electromagnetic (EM) energy 109 toward a target area 103 containing the material 101, a detector 105 for collecting scattered EM energy 110 reflected from the target area 103 due to the effect of the material 101 on the surrounding environment, and an analyzer 107 that analyzes the absorption spectrum of the collected scattered EM energy to detect the material 101. Additional details regarding transmitter 106, detector 105, and analyzer 107 are described below.

The illustrated system 100 includes a display 112 and user interface (UI) 124. Suitable displays 112 and user interfaces 124 will be understood by one of skill in the art from the description herein. It is contemplated that display 112 may include any display capable of presenting information including textual and/or graphical information. User interface 124 may be used to initiate remote target area detection for one or more locations in order to detect nuclear materials. In addition, user interface 124 may be used to select parameters provided to detector 105 for detection of nuclear materials. User interface 124 may further be used to select spectral measurement for display and/or storage. User interface 124 may include any suitable interface for initiating measurements and indicating storage and/or display of spectral information. User interface 124 may further include an input device such as a keypad for entering information.

The illustrated system 100 further includes a controller 111 and storage 125. Storage 125 may store absorption spectrum information and absorption spectrum signatures for one or more hazardous materials. Storage 125 may be a memory, a magnetic disk, a database or essentially any local or remote device capable of storing data. Controller 111 is configured to receive user inputs from user interface 124, such as measurement indicators, and display information on display 112. Controller 111 is also configured to control/implement transmitter 106, detector 105, and analyzer 107, responsive to user inputs received from user interface 124.

Further, controller 111 may also store spectrometry values for one or more measurement locations in storage 125. Moreover, controller 111 may be used to tune the transmitter 106 and the detector 105 to the same frequency and bandwidth, e.g., via a common laser. Controller 111 may be a conventional digital signal processor.

Radiation dose mapper (R.D.M.) 214 receives absorption spectrum information from analyzer 107 and determines a corresponding radiation dose value. The radiation dose may be stored in storage 125 and/or provided to display 112. In addition, radiation dose mapper 214 may arrange radiation doses for multiple locations as a spatial radiation dose map. The spatial radiation dose map may be stored in storage 125 and/or provided to display 112. Typically, the radiation is strongest (and thus has the greatest affect) next to the nuclear material and decays as the distance away from the nuclear material increases. Therefore, the radiation dose map may be used to indicate the direction and location of the concealed nuclear material. For example, a position having a peak radiation may indicate nuclear material located at that location.

It is contemplated that system 100 may be configured to connect to a global information network, e.g., the Internet, (not shown) such that the radiation dose map (and/or absorption spectrum information) may also be transmitted to a remote location for further processing and/or storage.

Figure 2:
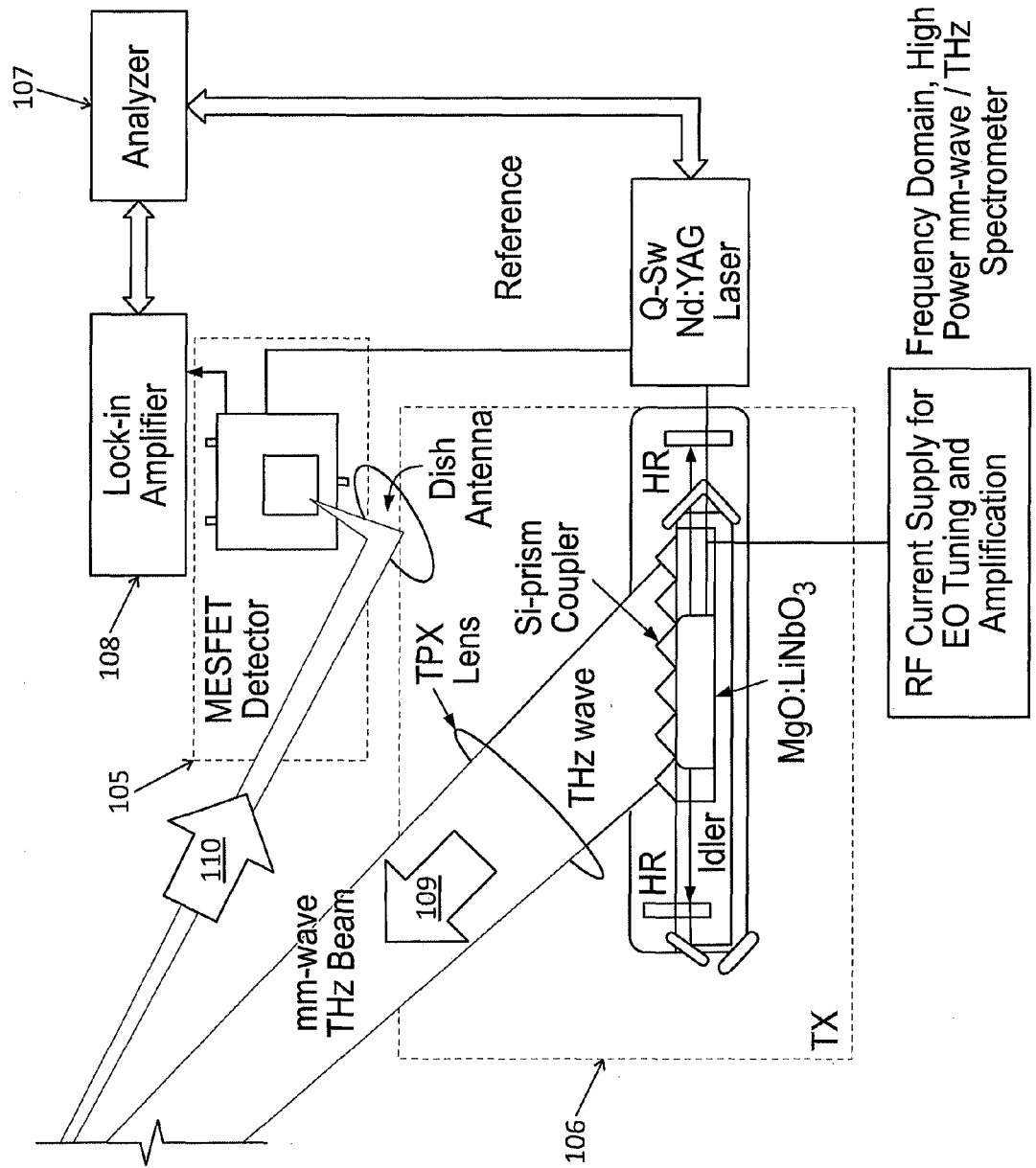
FIG. 2 is a schematic diagram illustrating an exemplary transmitter, detector, and analyzer (e.g., a computer) for use in the hazardous material detection system of FIG. 1.

FIG. 2 depicts an exemplary transmitter 106, detector 105, and analyzer 107. In one embodiment of the invention, the detector 105 may be a tunable mm-wave/infrared detector, and the scattered electromagnetic energy 110 may be a millimeter-wave/infrared beam.

Transmitter 106 is configured to transmit EM energy 109 (also referred to herein as a millimeter-wave/far-infrared beam 109) toward the target area. Transmitter 106 may be a frequency-tunable mm-wave/far-infrared signal generator that generates a millimeter-wave/far-infrared beam 109, e.g., having a frequency between about 50 GHz and about 3 THz. An antenna (e.g., a dish or parabolic antenna) may be used to direct the generated beam 109 toward the remote target area 103 (FIG. 1). Transmitter 106 may be tuned using an RF current supply. A suitable transmitter for use with the present invention is described in U.S. Pat. No. 7,995,628 to Wu, entitled RECYCLING PUMP-BEAM METHOD AND SYSTEM FOR A HIGH-POWER TERAHERTZ PARAMETRIC SOURCE, which is incorporated fully herein by reference. Alternative suitable transmitters will be understood by one of skill in the art from the description herein.

Detector 105 is configured to collect scattered EM energy 110 reflected from the remote target area 103 (FIG. 1). In the embodiment illustrated in FIG. 2, detector 105 is a metal semiconductor field effect transistor (MESFET) detector. Detector 105 may be synchronized with transmitter 106, e.g., by being referenced to a common laser. In the exemplary embodiment, the scattered electromagnetic energy 110 may be collected by detector 105 using an optional antenna (e.g., dish antenna).

Analyzer 107 is configured to analyze the absorption spectrum of the scattered EM energy 110 reflected from the target area to detect the presence of hazardous materials in the target area. Using the absorption spectrum of the collected scattered EM energy 110, the analyzer 107 may detect the presence of at least one hazardous material 101 (FIG. 1) in the remote target area 103 based on the analyzed absorbed spectrum. In one embodiment, analyzer 107 detects the presence of one or more hazardous materials by comparing the absorption spectrum to known signatures for hazardous materials (e.g., stored in storage 125 (FIG. 1)). If a match is identified, an indication of the hazardous material may be displayed by controller 111 (FIG. 1) on display 112. Suitable analyzers will be understood by one of skill in the art from the description herein.

In one embodiment, a lock-in amplifier 108 may be used to increase the signal-to-noise ratio. The lock-in amplifier 108 increases the signal-to-noise ratio by rejecting unwanted noise from the detected signal. Suitable lock-in amplifiers for use with the present invention will be understood by one of skill in the art from the description herein.

Referring back to FIG. 1, within optional enclosure 113, material 101 generates ionizing radiation, for example α-particles, β-particles, γ-rays, and neutrons. The ionizing radiation has sufficiently high energy to free electrons from molecules in enclosed atmosphere 115. The neutrons do not interact strongly with electrons, and so they cannot directly ionize atoms. However, they interact with atomic nuclei, producing ionizing nuclear recoils and secondary radioactive nuclei, which then emit ionizing radiation into the enclosed atmosphere 115.

Shielded enclosure 113 may represent any suitable container or barrier that may absorb most of the ionizing radiation to conceal the material 101. If nuclear material 101 is shielded by an enclosure 113 made of beryllium, lead, concrete, or water, most of the ionizing radiation and neutrons are absorbed. Remote detection of the low levels of escaping radiation is typically very difficult in the presence of effective shielding. Of the types of ionizing radiation generated by material 101, high energy γ-rays (e.g., with an energy greater than about 200 KeV) and fast neutrons may pass through enclosure 113.

Air 115 inside enclosure 113 may absorb heavy ionizing radiation, including the direct radiation and secondary radiation emitted by the atoms of the shielding materials after they are activated by nuclear radiation or neutrons. While shielded nuclear materials do not typically need to exchange air with outside atmosphere 114, shielded active nuclear facilities typically ventilate air 115. Accordingly, the ventilated air from inside enclosure 113 may contain rich ions which may be useful to detect active nuclear facilities. It is expected that the ventilated air contains rich ions, such as oxygen ions, but does not contain radioactive particles. These rich ions are added to the ions produced by radiation that passes through the shielding 113. Accordingly, these ventilated ions may be used in detecting and distinguishing active nuclear facilities.

As discussed above, it is possible for high energy γ-rays to pass through enclosure 113 into atmosphere 114. The γ-rays ionize in atmosphere 114 to produce ions 102, including both positive ions and negative ions 102. In general, the dominant ions 102 produced are $O_2+$ and $O_2-$.

Figure 3:
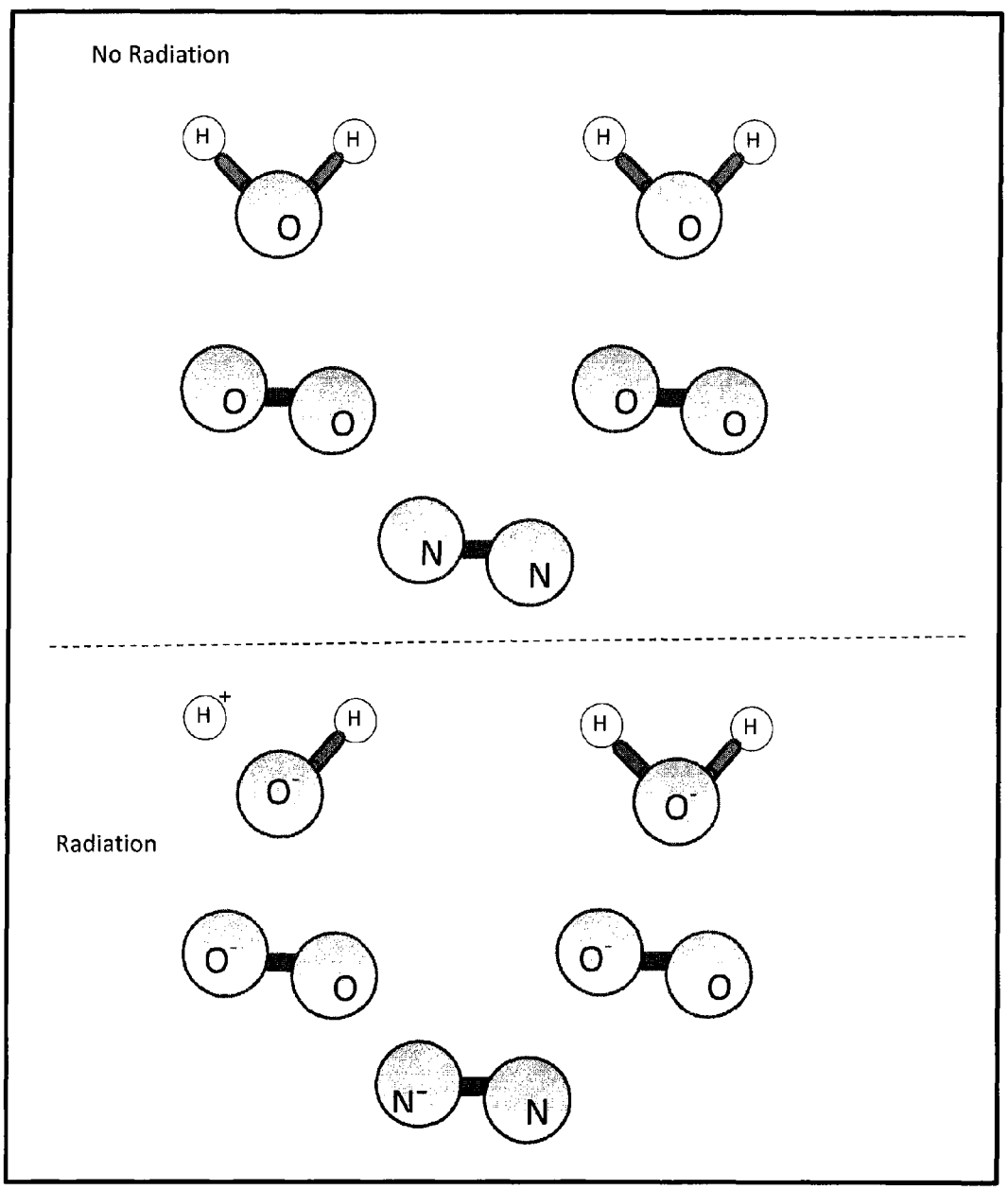
FIG. 3 is an illustration depicting known ionization resulting from radiation interacting with atmospheric molecules.

FIG. 3 depicts the ionization resulting from radiation interacting with atmospheric molecules (e.g., oxygen (O), nitrogen (N), and hydrogen (H)). The atmosphere is composed of a number of atmospheric molecules (78% nitrogen, 20.9% oxygen, 0.93% argon, 0.033% carbon dioxide, water molecules, etc.), and the ionization energy for each of these molecules is different.

In addition, each of the atmospheric molecules has different ionization cross-section, which varies depending on the ionization (or radiation energy). Although ionized air can be produced by other sources, such as corona discharge or high-voltage transmission lines, ionized air produced by nuclear materials has been shown to be distinguishable from the ionized air produced by the other sources (e.g. corona discharge).

As can be seen in FIG. 3, it is possible for the radiation energy to break the molecular bonds (for example, disassociate the hydrogen atoms from the oxygen atom in the water molecule) and form new gas molecules. The new gas molecules, such as ozone ($O_3$) and hydroxide ions (OH), alter the chemical composition of the local atmosphere. Since the production rate of positive and negative ions depend on the ionization source, the amount of positive and negative ions as well as new gas molecules found in the atmosphere can be used to determine the existence and type of nuclear material present in a target area 103 (FIG. 1).

FIG. 4 is a flow chart 400 illustrating exemplary steps for remotely detecting hazardous material in accordance with aspects of the invention. The steps of flow chart 400 are described using the systems described above with reference to FIGS. 1 and 2. Suitable alternative systems for implementing the present invention will be understood by one of skill in the art from the description herein and are considered within the scope of the present invention.

In block 402, EM energy is transmitted toward a target area. In an exemplary embodiment, transmitter 106 of system 100 (FIG. 1) is tuned to transmit EM energy 109 toward a remote target area 103. The EM energy may be a millimeter-wave and/or far-infrared frequency beam, e.g., between about 50 GHz and 3 THz. The transmitted EM energy is transmitted over a plurality of frequencies within frequency range, for example, between about 50 GHz and about 3 THZ (e.g., between about 1.5 THz and about 2 THz). In one embodiment, the transmitter 106 (FIG. 1) transmits the EM energy 109 at a level sufficient to make spectral measurements in a target area 103 more than 100 meters away. In another embodiment, the EM energy is generated at a level sufficient to make spectral measurements in a target area 103 more than a few hundred meters (possibly at least one kilometer) away.

In block 404, scattered EM energy 110 (FIG. 1) reflected by the target area 103 is collected. In an exemplary embodiment, the detector 105 (FIG. 1) of system 100 collects scattered electromagnetic energy 110 from the transmitted EM energy 109 that is reflected from the target area 103.

In block 406, the absorption spectrum of the collected EM energy is analyzed. In an exemplary embodiment, analyzer 107 (FIG. 1) analyzes the absorption spectrum of the collected scattered electromagnetic energy 110. As an optional step, the analyzer 107 may reject unwanted noise from the collected scattered electromagnetic energy 110.

Figure 5A:
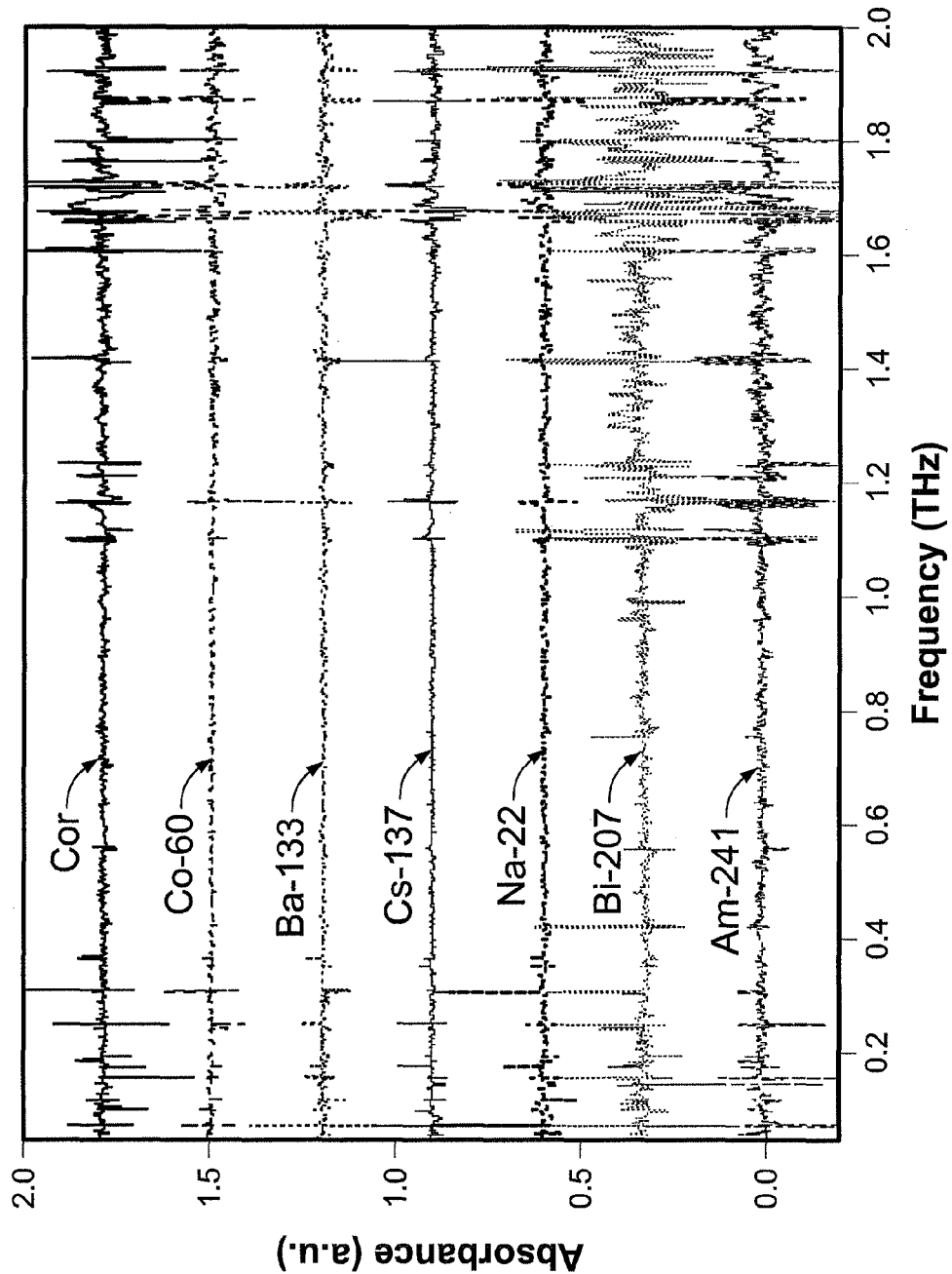
FIG. 5A is graph depicting a fully sampled terahertz spectrum of ionized air produced by corona discharge and various nuclear isotopes.
Figure 5B:
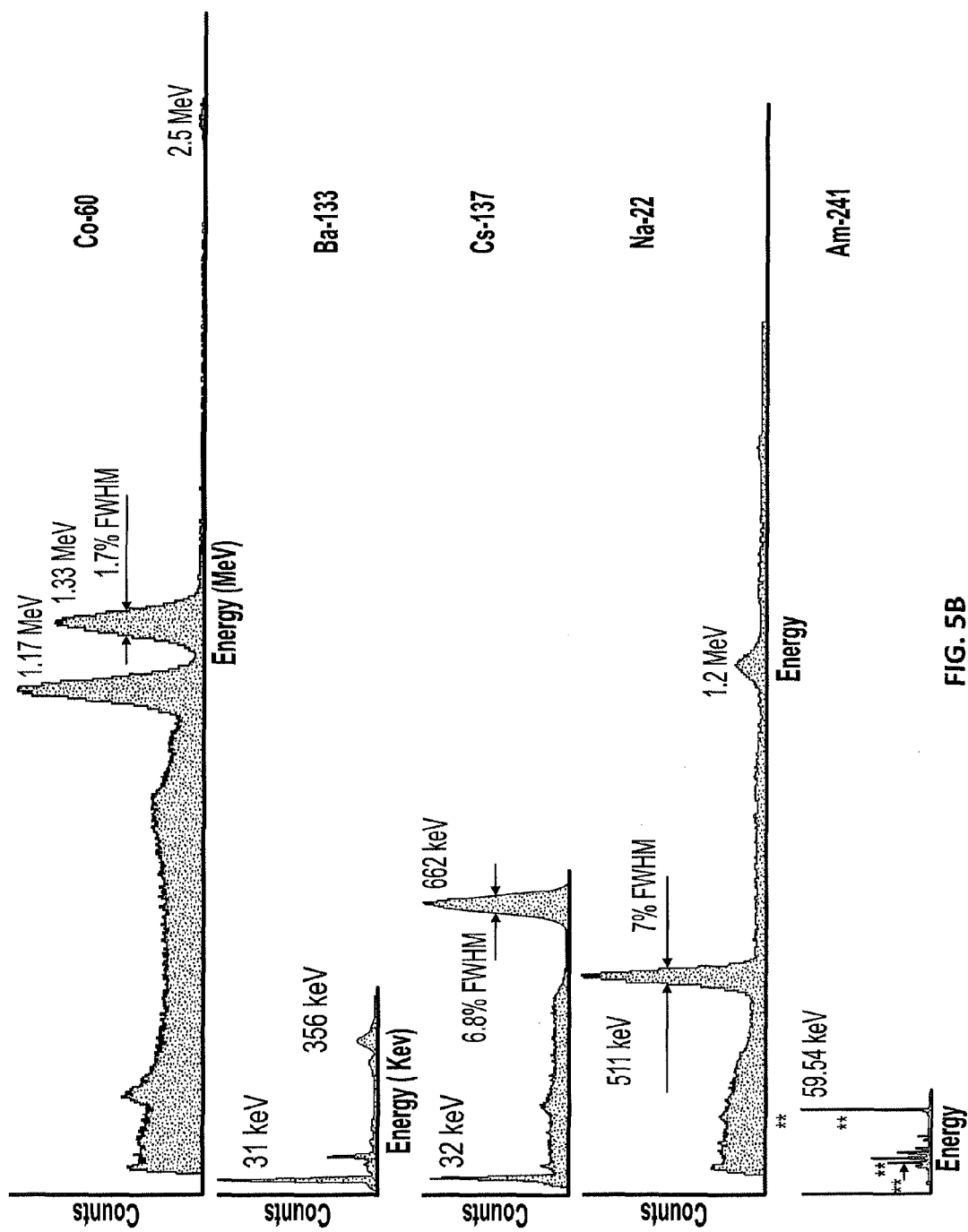
FIG. 5B is a graph depicting gamma energy spectra of the various nuclear isotopes in FIG. 5A.

In block 408, the presence of at least one hazardous material is detected. In an exemplary embodiment, analyzer 107 (FIG. 1) detects the presence or absence of at least one hazardous material 101 in the remote target area 103 based on the analyzed absorption spectrum. In one embodiment, analyzer 107 compares the absorption spectrum of the collected EM energy to the absorption spectrum of one or more known hazardous materials (e.g., the absorption spectrums of nuclear materials depicted in FIG. 5A). If there is a match, a hazardous material has been detected. FIG. 5A depicts a fully sampled terahertz spectrum of ionized air produced by various ionization sources including corona discharge and nuclear isotopes (Co-60, Ba-133, Cs-137, Na-22, Bi-207, and Am-241). In FIG. 5A, "Cor" means corona discharge. The terahertz spectrum depends on the gamma-ray energy spectrum of the nuclear isotope as depicted in FIG. 5B.

The indication of a presence of the detected hazardous material may thereafter be displayed, e.g., by controller 111 (FIG. 1) on display 112.

Figure 6:
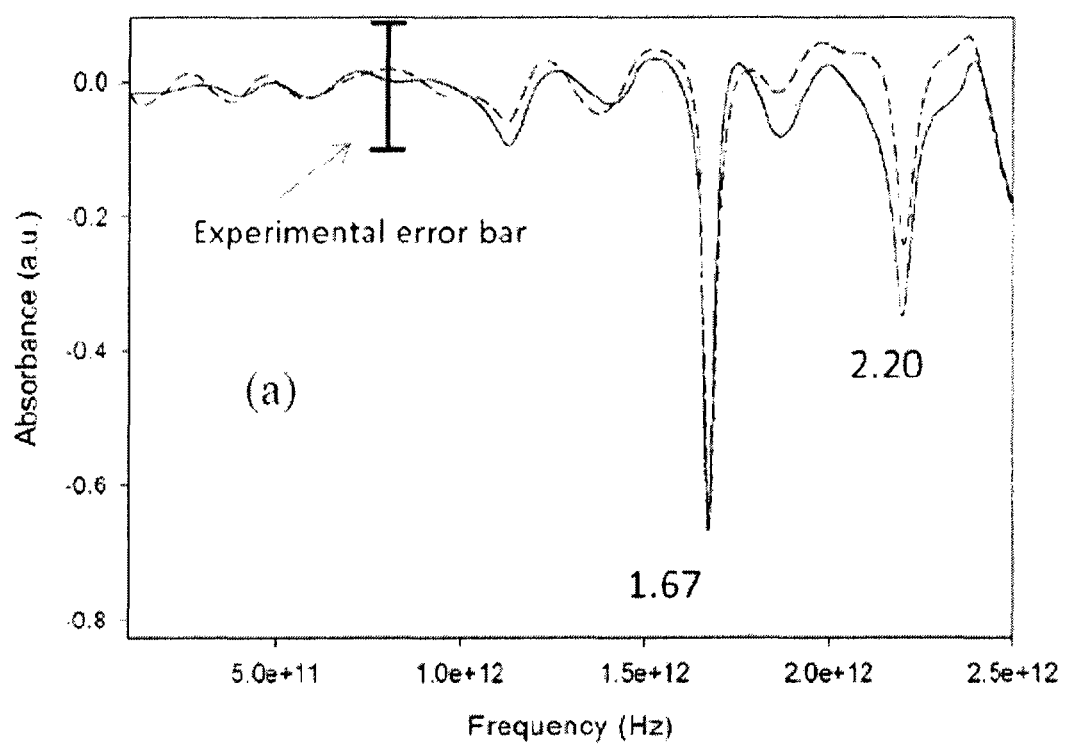
FIG. 6. is a graph depicting an under sampled terahertz spectrum of TNT vapor.

The system and methods as described in the exemplary embodiment for remotely detecting nuclear material can also be used to detect non-nuclear material. FIG. 6 illustrates under-sampled terahertz spectrum data for a non-nuclear material, evaporated TNT. The graph depicted in FIG. 6 illustrates two independent measurements (solid line and dashed line). Both measurements exhibit characteristic dips at 1.67 THz and 2.2 THz. Thus, the methods described herein can be used to remotely detect hazardous materials such as chemicals or explosive molecules in gas-phase using electromagnetic energy. As used herein, "under-sampled" means the frequency step interval is not as fine as the fully-sampled one. Typically "under-sampled" data are obtained with the frequency steps larger than several tens of GHz. For fully-sampled data, steps as fine as 0.5 GHz or finer may be used.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method for remotely detecting nuclear materials, the method comprising:
   transmitting electromagnetic energy in a frequency range of between about 50 GHz and about 3 THz toward a remote target area around an object;
   collecting the electromagnetic energy after it has interacted with and been modified by air in the remote target area around the object;
   analyzing an absorption spectrum of the collected modified electromagnetic energy in the frequency range of between about 50 GHz and about 3 THz to determine how the electromagnetic energy was modified by the air in the remote target area around the object;
   detecting whether the object comprises at least one nuclear material based on the modification to the electromagnetic energy by the air in the remote target area around the object; and
   identifying the nuclear material from the modified absorption spectrum if it is detected.

2. The method of claim 1, further comprising:
   rejecting noise present in the collected modified electromagnetic energy.

3. The method of claim 1, further comprising:
   displaying an indication of a presence of the at least one detected nuclear material.

4. The method of claim 1, wherein the transmitting step comprises:
   selectively transmitting the electromagnetic energy at a plurality of frequencies within a the frequency range.

5. The method of claim 4, wherein the frequency range is between about 1.5 THz and about 2 THz.

6. A system for remotely detecting nuclear material, wherein the system comprises:
   a transmitter that transmits electromagnetic energy in a frequency range of between about 50 GHz and about 3 THz toward a remote target area around an object;
   a detector that collects the electromagnetic energy after it has interacted with and been modified by air in the remote target area around the object;
   an analyzer that analyzes an absorption spectrum of the collected modified electromagnetic energy in the frequency range of between about 50 GHz and about 3 THz to determine how the electromagnetic energy was modified by the air in the remote target area around the object and detects whether the object comprises at least one nuclear material based on the modification to the electromagnetic energy by the air in the remote target area around the object.

7. The system of claim 6, further comprising:
   a lock-in amplifier that increases a signal-to-noise ratio by rejecting noise from the collected modified electromagnetic energy.

8. The system of claim 6, further comprising:
   a controller that tunes the transmitter and the detector to a same frequency and a same bandwidth.

9. The system of claim 6, further comprising:
   an interface that displays an indication of a presence of the detected at least one nuclear material.

10. A method for remotely detecting non-nuclear materials, the method comprising:
    transmitting electromagnetic energy in a frequency range of between about 50 GHz and about 3 THz toward a remote target area around an object;
    collecting the electromagnetic energy after it has interacted with and been modified by air in the remote target area around the object;
    analyzing an absorption spectrum of the collected modified electromagnetic energy in the frequency range of between about 50 GHz and about 3 THz to determine how the electromagnetic energy was modified by the air in the remote target area around the object; and
    detecting whether the object comprises at least one non-nuclear material based on the modification to the electromagnetic energy by the air in the remote target area around the object.

11. The method of claim 10, further comprising:
    rejecting noise present in the collected modified electromagnetic energy.

12. The method of claim 10, further comprising:
    displaying an indication of a presence of the at least one detected non-nuclear material.

13. The method of claim 10, wherein the transmitting step comprises:
    selectively transmitting the electromagnetic energy at a plurality of frequencies within the frequency range.

14. The method of claim 13, wherein the frequency range is between about 1.5 THz and about 2 THz.

15. The method of claim 10, wherein the non-nuclear material is a chemical agent.

16. The method of claim 10, wherein the non-nuclear material is a gas-phase explosive.

17. A system for remotely detecting non-nuclear material, wherein the system comprises:
    a transmitter that transmits electromagnetic energy in a frequency range of between about 50 GHz and about 3 THz toward a remote target area around an object;
    a detector that collects the electromagnetic energy after it has interacted with and been modified by air in the remote target area around the object;
    an analyzer that analyzes an absorption spectrum of the collected modified electromagnetic energy in the frequency range of between about 50 GHz and about 3 THz to determine how the electromagnetic energy was modified by the air in the remote target area around the object and detects whether the object comprises at least one non-nuclear material based on the modification to the electromagnetic energy by the air in the remote target area around the object.

18. The system of claim 17, further comprising:
a lock-in amplifier that increases a signal-to-noise ratio by rejecting noise from the collected modified electromagnetic energy.

19. The system of claim 17, further comprising:
a controller that tunes the transmitter and the detector to a same frequency and a same bandwidth.

20. The system of claim 17, further comprising:
an interface that displays an indication of a presence of the detected at least one non-nuclear material.

21. The system of claim 17, wherein the non-nuclear material is a chemical agent.

22. The system of claim 17, wherein the non-nuclear material is a gas-phase explosive.

\* \* \* \* \*

UNITED STATES PATENT AND TRADEMARK OFFICE
CERTIFICATE OF CORRECTION

PATENT NO. : 9,494,512 B2
APPLICATION NO. : 13/486560
DATED : November 15, 2016
INVENTOR(S) : Dong Ho Wu, Rongjia Tao and Benjamin D. Graber It is certified that error appears in the above-identified patent and that said Letters Patent is hereby corrected as shown below:

In the Specification

In Column 1, Line 16, the following paragraph should be added:
-- STATEMENT REGARDING FEDERALLY SPONSORED RESEARCH OR DEVELOPMENT
This invention was made with government support under HDTRA1-09-1-0038 awarded by the Defense Threat Reduction Agency. The government has certain rights in the invention. --

Signed and Sealed this
Twelfth Day of September, 2023

*Katherine Kelly Vidal*

Katherine Kelly Vidal
*Director of the United States Patent and Trademark Office*